United States Patent [19]

Hager et al.

[11] 4,190,049
[45] Feb. 26, 1980

[54] POSTERIOR LENS IMPLANT TOOL

[76] Inventors: Clarence L. Hager, 16037 Miami Way, Pacific Palisades, Calif. 90272; Ronald P. Jensen, 4156 Dorset Pl., Pasadena, Calif. 91103

[21] Appl. No.: 822,511

[22] Filed: Aug. 8, 1977

[51] Int. Cl.² ............................ A61F 9/00; A61F 1/16
[52] U.S. Cl. ..................................... 128/303 R; 3/13
[58] Field of Search ............... 128/303 R, 354, 355, 128/345; 3/13

[56] References Cited

U.S. PATENT DOCUMENTS

| | | | |
|---|---|---|---|
| 1,286,673 | 12/1918 | Linke | 128/354 |
| 2,834,023 | 5/1958 | Lieb | 3/13 |
| 3,817,078 | 6/1974 | Reed et al. | 128/354 |
| 3,913,148 | 10/1975 | Potthast | 128/303 R |
| 3,994,027 | 11/1976 | Jensen et al. | 3/13 |
| 4,041,552 | 8/1977 | Ganias | 3/13 |

FOREIGN PATENT DOCUMENTS 775701   5/1957   United Kingdom ............... 128/354

*Primary Examiner*—Lawrence W. Trapp

[57] ABSTRACT

A posterior lens implant tool for use in combination with an intraocular lens for implantation in the posterior chamber of the human eye. The intraocular lens includes a plano-convex lens, which is formed from an optical material that is suitable for an implantable lens. The plano-convex lens is adapted to be inserted into the posterior chamber of the human eye within the capsular membrane thereof. The intraocular lens also includes a pair of supporting loops which are formed from a material that is suitable for implantation into the eye, mechanically coupled to the peripheral edge of plano-convex lens and disposed at an angle in the range of 0° to 25° to the plane surface of the plano-convex lens so that their end portions are below the plane surface of the plano-convex lens. The posterior lens implant tool includes a pair of prongs, which are mechanically coupled together to form a pair forceps with each of the prongs having a tip which has a groove which is adapted to be secured to the inside surface of one of the supporting loops. The tip of each of the prongs is adaptedto secure the peripheral edge of the plano-convex lens.

2 Claims, 7 Drawing Figures

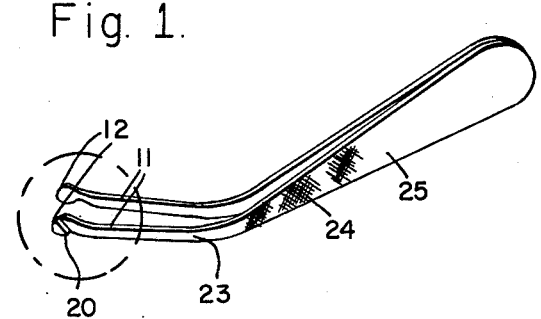
Fig. 1.
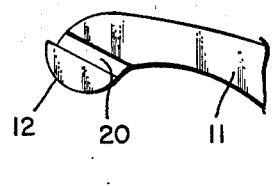
Fig. 2.
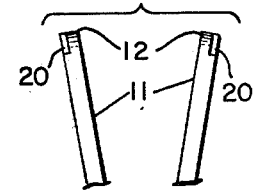
Fig. 3.
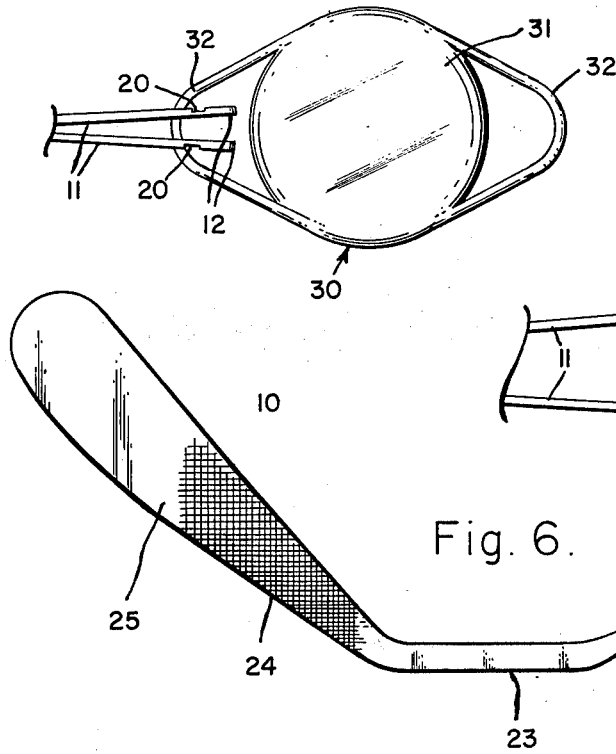
Fig. 4.
Fig. 5.
Fig. 6.
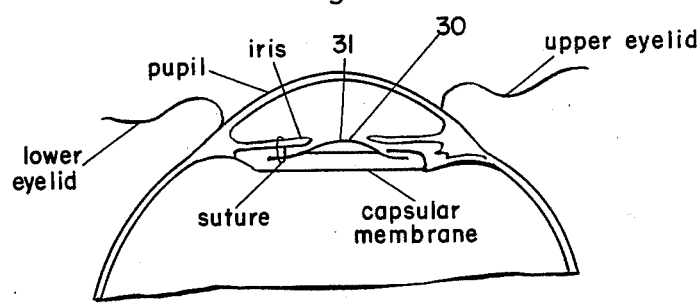
Fig. 7.

POSTERIOR LENS IMPLANT TOOL

BACKGROUND OF THE INVENTION

1. Field of the Invention

The present invention relates to an improved prepupillary lens which may be surgically implanted into the posterior chamber of the human eye and more particularly to an implant tool for implanting the lens into the posterior chamber.

2. Description of the Prior Art

In the prior art prepupillary lenses have been used in an operation for surgically implanting a lens on the iris of a human eye. Cornelius D. Binkhorst, M.D., who has performed this operation since 1958, has used a two-loop lens and a four-loop lens. He has described both of these lenses in an article entitled, "The Iridocapsular (Two-loop) Lens and the Iris-clip (Four-loop) Lens in Pseudophakia", which he wrote for the 1973 September-October edition of Transactions of the American Academy of Ophthalmology and Otolaryngology. These lenses are made from a plastic material, polymethyl methacrylate, which is commonly used to make contact lenses. The lenses are in the shape of a plano convex lens and have a diameter of 5.0 millimeters and a central thickness of from 0.5 millimeters to 0.6 millimeters depending on the required lens strength.

U.S. Pat. No. 3,994,027, entitled Prepupillary Lens for Implanting in a Human Eye, issued to Ronald P. Jensen and James Fetz on Nov. 30, 1976 teaches a two-loop lens which has its loops buried in the posterior chamber of the human eye, but which rests within the anterior chamber of the human eye. The difficulty with this position of the two-loop lens is that this is not the normal position of the original lens. The placement of the lens in the anterior chamber of the human eye is unnatural and creates a problem in the restoration of accurate binocular vision. Further the lens in the anterior chamber is not adjacent to the hyloid membrane for supporting the vitreous humor thereby making instances of forward displacement of the vitreous humor and retinal detachment more likely to occur.

U.S. Pat. No. 3,866,249, entitled Posterior Chamber Artificial Intraocular Lens, issued to Leonard Flom on Feb. 18, 1975, teaches an artificial intraocular lens for implantation in the posterior chamber of an eye which includes an optical zone portion fabricated of transparent material and shaped similar to a natural lens and a plurality of prongs attached to the optical zone portion near its periphery. The prongs protrude forwardly therefrom for insertion through the iris of the eye to hold and position the lens therein. The difficulty with this lens is that it is affixed to the iris of the eye and therefore it is not rigidly anchored thereby allowing the lens to move with eye movement. Subsequently, the iris may erode and the fixation of the lens may be lost. It would be far better to anchor the intraocular lens within the posterior chamber to the capsular membrane which is a very firm, non-viable tissue and which provides firm, secure and permanent fixation of the lens.

U.S. Pat. No. 3,711,870, entitled Artificial Lens Implant, issued to Rollin E. Deitrick on Jan. 23, 1973, teaches a lens for implantation in the eye which has a resilient flange that is sutured to the ciliary muscle of the eye to position and to retain the lens in the same position as the original lens. This lens irritates the ciliary body so that inflammation is likely to occur. The fixation of the lens to the ciliary body is not only a difficult surgical procedure, but also does not provide a firm, secure or permanent fixation of the lens.

U.S. Pat. No. 3,913,148, entitled Intraocular Lens Apparatus, issued to Ernst W. Potthast on Oct. 21, 1975, U.S. Pat. No. 3,991,426, entitled Posterior Chamber Artificial Intraocular Lens with Retaining Means and Instruments for Use Therewith, issued to Leonard Flom and Kenneth J. Rodgerson on Nov. 16, 1976, and U.S. Pat. No. 4,104,049, entitled Artificial Intraocular Lens and Supporting System Therefor, all teach intraocular lenses that are positioned in the posterior chamber of the eye and that are fixated to the iris of the eye.

The eye surgeon generally uses a pair of surgical forceps to grasp the supporting member of the intraocular lens as he is placing it into the eye. A standard pair of surgical forceps is efficient in placing intraocular lenses into the anterior chamber of the eye, but has been proven to be inefficient in placing the intraocular lenses into the posterior chamber of the eye.

One of the coinventors, Ronald P. Jensen, has already filed a patent application, entitled An Intraocular Lens for Implantation in the Posterior Chamber of a Human Eye, filed May 6, 1977, having Ser. No. 794,467 in which he taught an intraocular lens for implantation into the posterior chamber of a human eye.

Other embodiments of the intraocular lens may be made by substituting metal wire or supramid wire and by attaching the wire to the plano-convex lens by the methods taught in U.S. Pat. No. 3,994,027.

The difficulty with the insertion in the eyes of these intraocular lenses is that it is very difficult because the loops of the lenses cannot be grasped on their outside surfaces without injuring the eyes.

SUMMARY OF THE INVENTION

In view of the foregoing factors and conditions characteristic of the prior art it is a primary object of the present invention to provide a posterior lens implant tool for implanting an intraocular lens into the posterior chamber of a human eye.

It is another object of the present invention to provide a posterior lens implant tool that not only firmly secures the loops of the intraocular lens during implantation thereof, but which also easily disengages therefrom.

It is still another object of the present invention to provide a posterior lens implant tool that grasps the loops of the intraocular lens from within and not from without in order to minimize trauma to the eye during implantation therein.

It is yet another object of the present invention to provide a posterior lens implant tool to secure the intraocular lens in all degrees of freedom during insertion thereof.

It is yet still another object of the present invention to provide a posterior lens implant tool that may be inserted into a slit in the cornea at an angle that minimizes trauma to the eye during implantation of the intraocular lens.

In accordance with an embodiment of the present invention, a posterior lens implant tool for use in combination with an intraocular lens for implantation in the posterior chamber of the human eye is described. The intraocular lens includes a plano-convex lens, which is formed from an optical material that is suitable for an implantable lens. The plano-convex lens is adapted to be inserted into the posterior chamber of the human eye within the capsular membrane thereof. The intraocular lens also includes a pair of supporting loops which are formed from a material that is suitable for implantation into the eye, mechanically coupled to the peripheral edge of plano-convex lens and disposed at an angle in the range of 0° to 25° to the plane surface of the plano-convex lens so that their end portions are below the plane surface of the plano-convex lens. The posterior lens implant tool includes a pair of prongs, which are mechanically coupled together to form a pair of forceps with each of the prongs having a tip which has a groove which is adapted to be secured to the inside surface of one of the supporting loops. The tip of each of the prongs is adapted to secure the peripheral edge of the plano-convex lens.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a perspective view of a posterior lens implant tool which is constructed in accordance with the principles of the present invention.

FIG. 2 is a fragmentary elevational view of the tip of the posterior lens implant tool of FIG. 1.

FIG. 3 is a fragmentary top plan view of the tip of the posterior lens implant tool of FIG. 1.

FIG. 4 is a top plan view of an intraocular lens which is to be inserted into the posterior chamber of a human eye, having the posterior lens implant tool of FIG. 1 compressed to fit within one of the loops of the intraocular lens.

FIG. 5 is a top plan view of the intraocular lens of FIG. 4 having the posterior lens implant tool of FIG. 1 expanded to press against one of the loops of the intraocular lens.

FIG. 6 is a side elevational view of the posterior lens implant tool of FIG. 1 which is inserted into the posterior lens of FIG. 4.

FIG. 7 is a diagramatic view of a human eye showing the intraocular lens implanted in the posterior chamber of a human eye.

DESCRIPTION OF THE PREFERRED EMBODIMENT

In order to best understand the present invention a description of the preferred embodiment thereof is provided accompanied by a drawing. In FIG. 1 a perspective view of a posterior lens implant tool 10 for implanting an intraocular lens into the posterior chamber of a human eye is shown. The implant tool 10 includes a pair of prongs 11 which are mechanically coupled together to form a pair of forceps. Each prong includes a tip 12 having a groove 20 therein.

Referring to FIG. 2 in conjunction with FIG. 3 it can be noted that the tip 12 of each prong 11 has its groove 20 disposed in a downwardly sloping plane relative to the section of the prong 11 adjacent to the tip 12. The tip 12 of the prong 11 has a smooth outside surface which is interrupted only by the groove 20.

Referring again to FIG. 1 it can be noted that the implant tool 10 also includes a section 23 of each prong 11 which is disposed in substantially the same plane as its tip 12 and another section 24 which is disposed relative to the section 23 at an angle in the range of forty five to sixty five degrees (45° to 65°) and which also serves as the gripping point of the implant tool 10. The remaining portion 25 of each prong 11 is joined together to form a springing member so that the implant tool 10 may also serve as a pair of forceps.

In FIG. 4 intraocular lens 30 has a plano-convex lens 31, which is formed from an optical material that is suitable for an implantable lens, which is adapted to be inserted into the posterior chamber of the human eye within the capsular membrane thereof. The optical material most commonly used is polymethyl methacrylate. The intraocular lens 30 also has a pair of supporting loops 32, which are formed from a material that is suitable for implantation into the eye, mechanically coupled to the peripheral edge of the plano-convex lens 31 and disposed at an angle in the range of 0° to 25° to the plane surface of the plano-convex lens 11 so that their end portions are below the surface thereof.

Still referring to FIG. 4 the implant tool 10 is shown compressed so that its tips 12 may be inserted into the one of the supporting loops 32. Referring now to FIG. 5 the implant tool 10 is shown without being compressed so that the tips 12 of the pair of prongs 11 secures the peripheral edge of the plano-convex lens 31. Each tip 12 has a groove 20 which is adapted to be secured to the inside surface of one of the supporting loops 32.

Referring now to FIG. 6 the shape of the prongs 11 is adapted so that their tips 12 may be inserted into one of the supporting loops 32 and its adjacent section 23 may extend parallelly to the plane surface of the plano-convex lens 31 substantially in the same plane as the plano-convex lens 31 so that no portion of said adjacent section 23 extends above or below the intraocular lens 30.

The inventor-opthalmologist inserts this lens 30 through the iris of a human eye into the capsular membrane so that one of the first supporting loops 32 slides into the pocket of the capsular membrane. He then pulls the iris around the other of the supporting loops 32 so that the entire intraocular lens 30 can be placed into the posterior chamber of the human eye. He has then sutured the notch 14 of the other supporting loop 32 to the iris in order to provide a temporary securement to the iris for the intraocular lens 30. Once the posterior side and the anterior side of the pocket of the capsular membrane have scarred together there is no further need for suture coupling the other supporting loop 32 to the iris because the intraocular lens 10 is firmly, permanently and securely fixated to the capsular membrane. Furthermore the iris is free to function normally.

Referring now to FIG. 7 a schematic drawing of the intraocular lens 30 shows it after it has been implanted into the capsular membrane of a human eye. One should note that a portion of the capsular membrane has been removed so that the intraocular lens 30 may be inserted behind the iris. One of the supporting loops 32 is placed in a pocket of the remaining portion of the capsular membrane. The anterior side of this pocket and the posterior side of this pocket eventually scar together thereby securing the intraocular lens 30 within the posterior chamber.

From the foregoing it can be seen that a posterior lens implant tool for implanting an intraocular lens into the posterior chamber of the human eye has been provided. It should be noted that the sketches are not drawn to scale and that thicknesses and distances of and between figures are not to be considered significant.

Accordingly it is intended that the foregoing disclosure and showing made in the drawing shall be considered only an illustration of the principles of the present invention. The invention will be set out with particularity in the appended claims.

What is claimed is:

1. A posterior lens implant tool for use in combination with an intraocular lens for implantation in the posterior chamber of a human eye, said intraocular lens including:
    a. a plano-convex lens, which is formed from an optical material that is suitable for an implantable lens, which is adapted to be inserted into the posterior chamber of the human eye within the capsular membrane thereof; and
    b. a pair of supporting loops, which are formed from a material that is suitable for implantation into the eye, mechanically coupled to the peripheral edge of the plano-convex lens and disposed at an angle in the range of 0° to 25° to the plane surface of said plano-convex lens so that their end portions are below the plane surface of said plano-convex lens; said implant tool comprising:
    a. pair of prongs each of which has a tip and an adjacent section and which are mechanically coupled in order to form a pair of forceps;
    b. a first grooved means for securing the tip of each of said prongs to the inside surface of one of the supporting loops; and
    c. second groove means for securing the tip of each said prongs to the peripheral edge of the plano-convex lens whereby each of said prongs is adapted so that its said tip may be inserted into one of the supporting loops and its said adjacent section may extend parallelly to the plane surface of the plano-convex lens substantially in the same plane as the plano-convex lens so that no portion of its said adjacent section extends above or below the intraocular lens.

2. A posterior lens implant tool according to claim 1 wherein the remainder of each of said prongs is disposed at an angle in the range of forty-five to sixty-five degrees to its said adjacent section.

* * * * *